United States Patent
Gonenc et al.

(10) Patent No.: US 11,278,361 B2
(45) Date of Patent: Mar. 22, 2022

(54) SENSORS FOR TOUCH-FREE CONTROL OF SURGICAL ROBOTIC SYSTEMS

(71) Applicant: Verb Surgical Inc., Mountain View, CA (US)

(72) Inventors: Berk Gonenc, Cupertino, CA (US); Xin Liu, Milpitas, CA (US); Bernhard A. Fuerst, Sunnyvale, CA (US); Jose Luis Cordoba, Malaga (ES); Pablo E. Garcia Kilroy, Menlo Park, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 90 days.

(21) Appl. No.: 16/418,726

(22) Filed: May 21, 2019

(65) Prior Publication Data

US 2020/0367978 A1    Nov. 26, 2020

(51) Int. Cl.
| | | |
|---|---|---|
| A61B 34/30 | (2016.01) | |
| A61B 90/50 | (2016.01) | |
| G06F 3/044 | (2006.01) | |
| G06F 3/01 | (2006.01) | |
| A61B 17/00 | (2006.01) | |

(52) U.S. Cl.
CPC .............. *A61B 34/30* (2016.02); *A61B 90/50* (2016.02); *G06F 3/017* (2013.01); *G06F 3/0444* (2019.05); *G06F 3/0446* (2019.05); *A61B 2017/00207* (2013.01); *A61B 2562/0257* (2013.01); *G06F 2203/04108* (2013.01)

(58) Field of Classification Search
CPC ......... A61B 34/30–34/37; A61B 34/70–34/77; A61B 90/50; A61B 2017/00207; A61B 2562/0257; G06F 3/0446; G06F 3/0444; G06F 3/017; G06F 2203/04108
See application file for complete search history.

(56) References Cited

U.S. PATENT DOCUMENTS

| 7,570,064 B2 | 8/2009 | Roziere |
| 8,269,176 B2 | 9/2012 | D'Ambrosio et al. |

(Continued)

FOREIGN PATENT DOCUMENTS

| EP | 1 324 364 A2 | 2/2003 |
| WO | 2006/124390 A2 | 11/2006 |

(Continued)

OTHER PUBLICATIONS

International Search Report & Written Opinion of the International Searching Authority dated Feb. 18, 2020, for PCT application No. US2019/034718.
Feasibility of touch-less control of operating room lights, by Florian Harmann and Alexander Schlaefer; International Journal of Computer Assisted Radiology and Surgery; vol. 8, Issue 2, pp. 259-268; Mar. 2013.

(Continued)

*Primary Examiner* — Jonathan T Kuo
(74) *Attorney, Agent, or Firm* — Womble Bond Dickinson (US) LLP

(57) ABSTRACT

A control system for surgical robots based on proximity sensing, the control system including a proximity sensor coupled to a component of a surgical robot, the surgical robot component including a table, robotic arms coupled to the table, and surgical tools mounted on the robotic arms, the proximity sensor configured to sense a movement of a nearby controlling object in one or more degrees of freedom; and a processor configured to drive the component of the surgical robot to follow the movement of the controlling object.

18 Claims, 8 Drawing Sheets

(56) References Cited

U.S. PATENT DOCUMENTS

| | | | |
|---|---|---|---|
| 8,816,628 | B2 | 8/2014 | Nowlin et al. |
| 9,323,398 | B2 | 4/2016 | Bernstein et al. |
| 9,579,793 | B2 | 2/2017 | Jacob et al. |
| 9,914,211 | B2* | 3/2018 | Hynna .................. A61B 34/20 |
| 10,022,195 | B2* | 7/2018 | Scholan ................. A61B 34/37 |
| 2013/0244731 | A1* | 9/2013 | Oishi .................... G06F 3/0416 |
| | | | 455/566 |
| 2013/0325029 | A1 | 12/2013 | Hourtash et al. |
| 2015/0038981 | A1 | 2/2015 | Kilroy et al. |
| 2016/0270867 | A1* | 9/2016 | Scholan ................. A61B 34/37 |
| 2017/0252921 | A1* | 9/2017 | Hynna .................. A61B 90/98 |
| 2017/0258534 | A1 | 9/2017 | Hourtash et al. |
| 2017/0296277 | A1 | 10/2017 | Hourtash et al. |
| 2018/0078319 | A1 | 3/2018 | Nobles et al. |
| 2018/0092706 | A1 | 4/2018 | Anderson et al. |
| 2018/0161108 | A1 | 6/2018 | Savall et al. |
| 2018/0177523 | A1 | 6/2018 | Piron et al. |
| 2018/0288515 | A1 | 10/2018 | Peterson et al. |
| 2018/0344559 | A1* | 12/2018 | Hoel .................... B60B 33/0018 |
| 2019/0005848 | A1 | 1/2019 | Garcia Kilroy et al. |

FOREIGN PATENT DOCUMENTS

| | | |
|---|---|---|
| WO | WO201620052 A1 | 2/2016 |
| WO | WO 2016/082019 A1 | 6/2016 |
| WO | 2018/052795 A1 | 3/2018 |
| WO | WO2018148845 A1 | 8/2018 |

OTHER PUBLICATIONS

Thracker—Using Capacitive Sensing for Gesture Recognition, by Raphael Wimmer, Paul Holleis, Matthias Kranz, Albrecht Schmidt; Proceedings of the 26th IEEE International Conference on Distributed Computing Systems Workshops (ICDCSW'06) 0-7695-2541-5/06; 2006; 6 pages.

A Capacitance Based Proximity Sensor for Whole Arm Obstacle Avoidance, by J. L Novak and J. T. Feddema; Proceedings 1992 IEEE International Conference on Robotics and Automation; 1992; 23 Pages.

International Preliminary Report on Patentability for International Application No. PCT/US2019/034718 dated Dec. 2, 2021, 9 pages.
International Preliminary Report on Patentability for International Application No. PCT/US2019/034719 dated Dec. 2, 2021, 9 pages.

* cited by examiner

SENSORS FOR TOUCH-FREE CONTROL OF SURGICAL ROBOTIC SYSTEMS

BACKGROUND

Field

Embodiments related to robotic systems, are disclosed. More particularly, embodiments related to surgical robotic systems and corresponding methods for touch-free control of surgical robotic system components, are disclosed.

Background Information

Endoscopic surgery involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted tools. For example, surgical robotic manipulators, including surgical tools, may be mounted to a surgical table. Prior to performing a surgical procedure, the surgical robotic manipulator and/or the surgical table must be moved to the appropriate position for the desired procedure. In addition, in some cases, the surgical robotic manipulator and/or surgical table may need to be moved during a procedure. Typically, these types of surgical robotic system components are moved manually by the user applying force directly the component. Due to the initial position of the surgical robotic manipulator and/or the surgical table (e.g., the surgical robotic manipulator may be folded below the surgical table), however, it can be difficult for the user (e.g., surgeon or assistant) to manually move these components smoothly within the operating arena, and while still maintaining desired safety and sterility conditions.

SUMMARY

A surgical robotic system may include a surgical robotic system component, for example a surgical robotic manipulator (e.g., a surgical robotic arm) including a number of links which are connected to one another by joints. It is imperative that the surgical robotic arm and associated joints be capable of fluid motion and easily controlled. For example, in the case of a surgical robotic manipulator, such as robotic arm connected to a surgical table, at least a portion of the surgical robotic arm may be collapsed or stowed under the surgical table. Prior to beginning a surgical procedure, the surgical robotic arm may be manually reconfigured from the stowed position to an operating position. When the surgical robotic manipulators are folded under the surgical table, however, it may difficult for the user to reach and have a strong grasp of the manipulator while trying to deploy the arm and position it over the surgical table. In addition, surgical robotic system components such as surgical robotic manipulators are often covered with drapes to maintain sterility. Holding the surgical robotic manipulators over drapes and manually pulling/pushing them around, however, may trap the drape between links and tear it, which breaks sterility. In addition, physically touching or grasping the surgical robotic manipulator and moving it may cause injuries, for example, the user may pinch a finger between the links. Moreover, as a practical matter, dragging the robot to a desired pose by manual force is not easy, and may lead to discretized and jagged movement of the manipulator. The instant invention therefore proposes a system in which surgical robotic manipulators can be moved or reconfigured without the user needing to physical touch the surgical robotic manipulator, or otherwise apply a direct force to the surgical robotic manipulator.

Representatively, in one aspect, the invention is directed to a sensor assembly that is coupled to the surgical robotic system component and is made up of multiple capacitive hover sensing pads that allow for touch-free or non-contact sensing of the user's hand/finger gestures. For example, the capacitive hover sensing pads can be arranged in several different configurations to sense motion in various directions. For example, in one aspect, the multiple hover sensing pads may be in a grid like pattern made up of a number of horizontal conductive pad lines and vertical conductive pad lines that cross the horizontal conductive pad lines to form the grid pattern. A change of capacitance on each linear conductive pad line, as caused, for example, by user hand gestures (e.g., moving left and right, or up and down, relative to the sensor assembly) can be detected. In another embodiment, the capacitive hover sensing pads may be arranged in a pie-shaped pattern, which is configured to detect not only translation of the user's hand (linear motion) but also rotational user gestures (angular motion) in the three-dimensional space above the capacitive hover sensing pads. The gestures and/or hand movements detected by the sensor assembly may then be output as a signal to a control system or processing component that processes the signal and causes the surgical robotic manipulator to move in parallel.

In one aspect, the sensor assembly is built into the surgical robotic system component, for example, a surgical robotic arm link so that the link has a sense of its surroundings. By holding a hand close to the link of the surgical robotic arm, the user can control the movement of the surgical robotic arm without having to physically touch the surgical robotic system or apply any force on the links. In addition, gestures may be programmed to perform more sophisticated robotic tasks and further facilitate easy/safe user-robot interaction. For example, a surgical robotic arm link closer to the end effector may be programmed to sense a hand gesture and to guide the surgical robotic arm to switch between predefined poses.

This type of touch-free control over a surgical robotic system component provides several advantages. For example, touch-free control of a surgical robotic system component improves ergonomics by giving the operator better flexibility in terms of where to stand and handle the surgical robotic system component without having to worry about the overall pose of the surgical robotic system component and having to spend significant physical effort due to robot's inherent inertia (mass, joint friction). In addition, to bring a surgical robotic system component such as a surgical robotic arm from one position to another following a desired trajectory, a continuous movement of the surgical robotic arm linkages by simply dragging the surgical robotic arm is difficult to achieve due to anisotropy (varying friction and inertia of robot joints). Moreover, to follow a smooth trajectory, more than one arm joint may need to be activated at the same time with varying speeds. As a result, physically touching and pushing/pulling the surgical robotic arm typically results in an arm motion that is jagged and discretized due to stick/slip action at each joint. In addition, in some configurations, it may happen that no single joint is aligned in the correct orientation to provide a motion in the desired direction, thus the arm starts moving off the desired trajectory when pushed/pulled. Therefore, the user usually needs to think about every joints' degree of freedom and account for link lengths/joint limits to come up with a feasible plan to bring the robot to a target pose.

The instant invention solves these issues by including proximity sensor (e.g., a capacitive hover sensing assembly) in the surgical robotic system component which allows for touch-free movement of the component without the user having to think about the complex kinematics. The sensor assembly allows the user to move the surgical robotic system component, for example a surgical robotic arm with end effector, to the desired pose while the required joint movement(s) for this command are automatically computed by the robotic system. The resulting motion is therefore smooth and continuous. Representatively, in one aspect, the information obtained from the capacitive hover sensing assembly can be used in a position control loop to move the surgical robotic system component to a desired pose. For example, in one aspect, the difference between a preset desired distance/position/pose from the sensor and the instantaneous measured distance/position/pose of user's hand is fed back to the surgical robotic system component as the command input. The command input is then used to control the movement of a surgical robotic system component having a single degree of freedom (DOF) or multiple DOF. For example, by moving the finger back and forth near the sensor assembly coupled to the component, and commanding the system to preserve a fixed offset from the sensed finger location, the operator can move the component in parallel to the finger, for example, up and down, or left and right, by moving finger(s) in space without any touch. The same concept can be extended to move a multi-DOF surgical robotic system component such as a surgical robotic arm or surgical table, according to multiple degrees of freedom (e.g., a up/down, right/left, forward/back, yaw, pitch or roll).

Representatively, in one aspect, the invention is directed to a control system for surgical robots based on proximity sensing including a proximity sensor coupled to a component of a surgical robot, the surgical robot component including a table, robotic arms coupled to the table, and surgical tools mounted on the robotic arms, the proximity sensor configured to sense a movement of a nearby controlling object in one or more degrees of freedom; and a processor configured to drive the component of the surgical robot to follow the movement of the controlling object. In some aspects, at least one or more degrees of freedom comprise at least a linear movement along a z-axis, an x-axis and a y-axis and an angular movement within an x-y plane parallel to the proximity sensor. The proximity sensor may be operable to sense a movement of the nearby controlling object according to at least five degrees of freedom. The surgical robot may include robotic arms and the support member is a cosmetic panel of at least one of the robotic arms that faces away from the surgical table. In some cases, the proximity sensor comprises conductive regions printed onto the cosmetic panel of the robotic arm. In still further aspects, the surgical robot component is a table and the proximity sensor comprises a support member that forms a vertically oriented side panel of the table that connects to a horizontally oriented patient support surface of the table. The proximity sensor may include a first set of capacitive lines and a second set of capacitive lines printed in a grid pattern on a support member, wherein the first set of capacitive lines and the second set of capacitive lines are operable to detect a linear movement of the object. The proximity sensor may include a plurality of capacitive pads arranged in a circular shape, and the plurality of capacitive pads are configured to detect an angular movement of the controlling object around the circular shape.

In still further aspects, a surgical robotic system is disclosed and includes a surgical robot component having multiple degrees of freedom; a proximity sensor coupled to the surgical robot component, the proximity sensor comprising a plurality of sensing pads operable to detect a linear movement and an angular movement of a nearby controlling object prior to contact with the surgical robot component; and a processor configured to drive the surgical robot component to follow the movement of the controlling object. The linear movement may include a movement in a direction parallel to a z-axis, an x-axis or a y-axis and the angular movement comprises a rotational movement about the z-axis, the x-axis or the y-axis. The plurality of sensing pads may be capacitive sensing pads printed on a surface of the surgical robot component. The surgical robot component may include a robotic arm and the processor is operable to control a movement of the robotic arm according to at least four degrees of freedom that are in parallel to the detected movement of the controlling object and maintain a same distance from the controlling object. The robotic arm may include a plurality of links coupled to one another by a plurality of joints, and the processor is operable to cause a movement of at least two of the plurality of joints to move the robotic arm in parallel to the controlling object. The surgical robot component may include a surgical table and the processor is operable to drive a movement of the table between a first position and a second position. The processor may be operable to cause the surgical robot component to maintain a same distance from the controlling object by measuring an actual distance between the surgical robot component and the controlling object and comparing the actual distance to a predetermined distance, and when the actual distance is different than the predetermined distance, sending a robotic command signal to the surgical robot component causing the surgical robot component to move in the same direction as the controlling object until the actual distance is the same as the predetermined distance.

In additional aspects, a method for touch-free control of a surgical robot component based on proximity sensing is disclosed. The method may include determining a distance between a user and a surgical robot component using a proximity sensor coupled to the surgical robot component; comparing the determined distance of the user to a predetermined target distance, the predetermined target distance being a desired distance to be maintained between the user and the surgical robot component; and automatically causing the surgical robot component to move based on the comparing so that the determined distance is equal to the predetermined target distance prior to the user contacting the surgical robot component. The proximity sensor may be operable to detect a linear movement of the user or an angular movement of the user, and the surgical robot component is caused to move in parallel to the linear movement or the angular movement. The proximity sensor may include a plurality of capacitive pads, and the linear movement and the angular movement are detected based on a change in capacitance at one or more of the plurality of capacitive pads. The surgical robot component may be a robotic arm and the robotic arm is caused to move according to a number of degrees of freedom so that the determined distance is equal to the predetermined target distance. The surgical robot component may be caused to move in a same direction as the user so that the determined distance is equal to the predetermined target distance.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Figure 1:
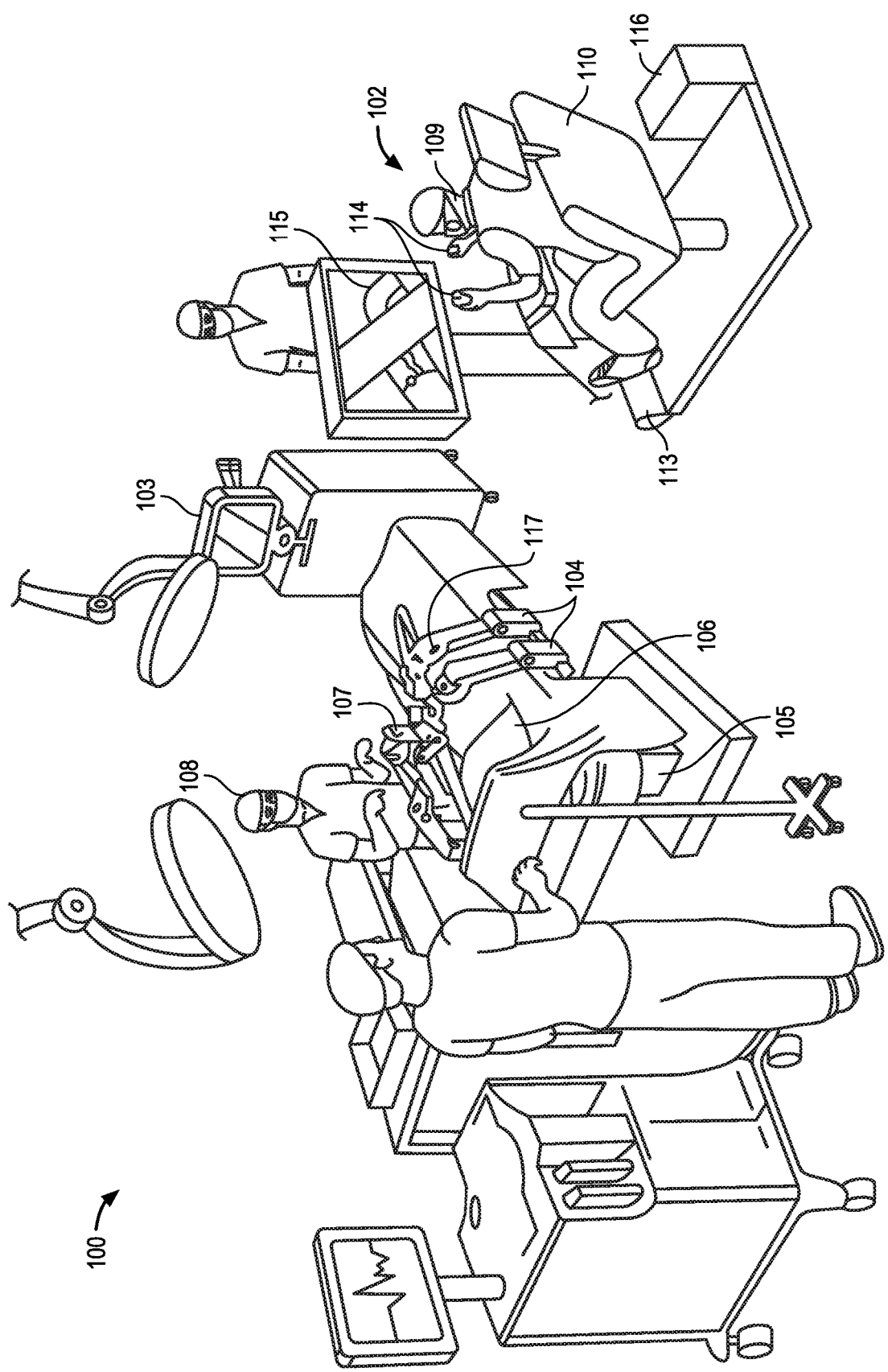
FIG. 1 is a pictorial view of an example surgical robotic system in an operating arena, in accordance with an embodiment.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

In addition, the terminology used herein is for the purpose of describing particular aspects only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Moreover, the use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of any particular surgical robotic system component to a specific configuration described in the various embodiments below.

Referring to FIG. 1, this is a pictorial view of an example surgical robotic system 100 in an operating arena. The surgical robotic system 100 includes a user console 102, a control tower 103, and one or more surgical robotic arms 104 at a surgical robotic platform 105, e.g., a table, a bed, etc. The system 100 can incorporate any number of devices, tools, or accessories used to perform surgery on a patient 106. For example, the system 100 may include one or more surgical tools 107 used to perform surgery. A surgical tool 107 may be an end effector that is attached to a distal end of a surgical arm 104, for executing a surgical procedure.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 107 is a grasper that can grasp tissue of the patient. The surgical tool 107 may be controlled manually, by a bedside operator 108; or it may be controlled robotically, via actuated movement of the surgical robotic arm 104 to which it is attached. The robotic arms 104 are shown as a table-mounted system, but in other configurations the arms 104 may be mounted in a cart, ceiling or sidewall, or in another suitable structural support.

Generally, a remote operator 109, such as a surgeon or other operator, may use the user console 102 to remotely manipulate the arms 104 and/or the attached surgical tools 107, e.g., teleoperation. The user console 102 may be located in the same operating room as the rest of the system 100, as shown in FIG. 1. In other environments however, the user console 102 may be located in an adjacent or nearby room, or it may be at a remote location, e.g., in a different building, city, or country. The user console 102 may comprise a seat 110, foot-operated controls 113, one or more handheld user input devices, UID 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the arms 104 and the surgical tools 107 (that are mounted on the distal ends of the arms 104.)

In some variations, the bedside operator 108 may also operate the system 100 in an "over the bed" mode, in which the bedside operator 108 (user) is now at a side of the patient 106 and is simultaneously manipulating a robotically-driven tool (end effector as attached to the arm 104), e.g., with a handheld UID 114 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the robotic system 100 are in a stowed configuration or withdrawn configuration (to facilitate access to the surgical site.) Once access is completed, initial positioning or preparation of the robotic system 100 including its arms 104 may be performed. Next, the surgery proceeds with the remote operator 109 at the user console 102 utilizing the foot-operated controls 113 and the UIDs 114 to manipulate the various end effectors and perhaps an imaging system, to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the robotic arms 104. Non-sterile personnel may also be present to assist the remote operator 109 at the user console 102. When the procedure or surgery is completed, the system 100 and the user console 102 may be configured or set in a state to facilitate post-operative procedures such as cleaning or sterilization and healthcare record entry or printout via the user console 102.

In one embodiment, the remote operator 109 holds and moves the UID 114 to provide an input command to move a robot arm actuator 117 in the robotic system 100. The UID 114 may be communicatively coupled to the rest of the robotic system 100, e.g., via a console computer system 116. The UID 114 can generate spatial state signals corresponding to movement of the UID 114, e.g. position and orientation of the handheld housing of the UID, and the spatial state signals may be input signals to control a motion of the robot arm actuator 117. The robotic system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment or link of the arm 104, the movement of a corresponding surgical tool that is attached to the arm may mimic the movement of the UID 114. Similarly, interaction between the remote operator 109 and the UID 114 can generate for example a grip control signal that causes a jaw of a grasper of the surgical tool 107 to close and grip the tissue of patient 106.

The surgical robotic system 100 may include several UIDs 114, where respective control signals are generated for each UID that control the actuators and the surgical tool (end effector) of a respective arm 104. For example, the remote operator 109 may move a first UID 114 to control the motion of an actuator 117 that is in a left robotic arm, where the actuator responds by moving linkages, gears, etc., in that arm 104. Similarly, movement of a second UID 114 by the remote operator 109 controls the motion of another actuator 117, which in turn moves other linkages, gears, etc., of the robotic system 100. The robotic system 100 may include a right arm 104 that is secured to the bed or table to the right side of the patient, and a left arm 104 that is at the left side of the patient. An actuator 117 may include one or more motors that are controlled so that they drive the rotation of a joint of the arm 104, to for example change, relative to the patient, an orientation of an endoscope or a grasper of the surgical tool 107 that is attached to that arm. Motion of several actuators 117 in the same arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106.

In some aspects, the communication between the platform 105 and the user console 102 may be through a control tower 103, which may translate user commands that are received from the user console 102 (and more particularly from the console computer system 116) into robotic control commands that transmitted to the arms 104 on the robotic platform 105. The control tower 103 may also transmit status and feedback from the platform 105 back to the user console 102. The communication connections between the robotic platform 105, the user console 102, and the control tower 103 may be via wired and/or wireless links, using any suitable ones of a variety of data communication protocols. Any wired connections may be optionally built into the floor and/or walls or ceiling of the operating room. The robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
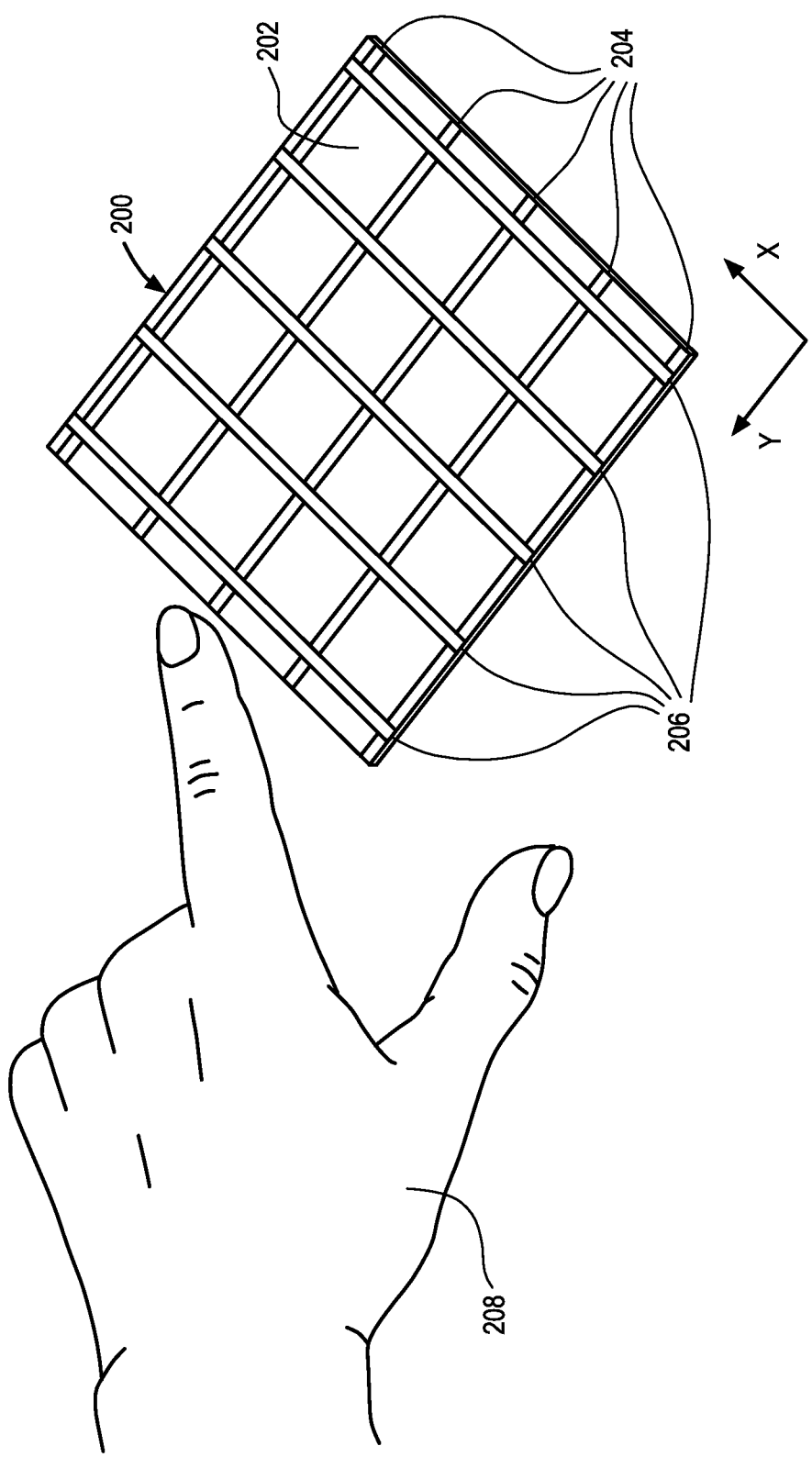
FIG. 2 is a pictorial view of a capacitive hover sensing assembly, in accordance with an embodiment.

FIG. 2 is a pictorial view of a sensing assembly that can be integrated into one or more surgical robotic system components of surgical robotic system 100. Sensing assembly 200 may be any type of sensing assembly suitable for detecting the movement of a controlling object, for example, a proximity sensor, a capacitive hover sensor, or the like. Representatively, sensing assembly 200 may be a capacitive hover sensing assembly that includes a support member 202 with one or more capacitive members 204, 206. Capacitive members 204, 206 may be made of any sort of conductive material that allows for capacitive sensing of an object near the sensor without any portion of the object physically touching the sensor (i.e. in the absence of pressure). Capacitive members 204, 206 may be referred to herein as capacitive pads, capacitive regions, capacitive lines, or the like, depending on their particular size, shape and/or configuration with respect to the support member. Representatively, each of capacitive members 204, 206 may be made of a copper material that is formed on, in, or otherwise coupled to support member 202, which can be any structure made of an insulating material (e.g., plastic, ceramic, etc.). As will be discussed in more detail in reference to FIG. 4, the entire assembly 200, support member 202 and/or capacitive members 204, 206 may be integrated into a component of the surgical robotic system. For example, the capacitive members 204, 206 may be made of a conductive material that is printed directly onto a surface (i.e., support member) of the surgical robotic system component, for example, they may be printed on a cosmetic panel or outer shell of a surgical robotic arm. In some aspects, the support member 202 forms the cosmetic panel or outer shell of the surgical robotic component. It should therefore be understood that sensing assembly 200 is not intended to be limited to a flat plane, or any other shape/size, rather it can be formed or manufactured to have any size and shape suitable for use with any surgical robotic system component.

Application of a voltage to the capacitive members 204, 206 results in the formation of an electrostatic field at each of the capacitive members 204, 206. When an object 208 that is conductive or has a dielectric constant different than air, for example any portion of a user's hand, is brought within a detection range of the capacitive members 204, 206, it changes the local electric field, and in turn the capacitance at each of members 204, 206. This change in capacitance at each of the capacitive members 204, 206 can be sensed by assembly 200 and output as a sensor signal to a controller/processor of surgical robotic system 100 to determine/measure the proximity, location, position, displacement, movement or the like, of object 208 with respect to assembly 200, and any surgical robotic system component that sensor assembly 200 is coupled to. The controller/processor can, in turn, determine a desired proximity, location, position, displacement, movement or the like, of the surgical robotic system component based on the information detected by assembly 200 and move the surgical robotic system component in parallel to the object 208, without direct contact between the object 208 and the component. It should be understood that the term "parallel" to describe the surgical robotic system component movement is intended to mean that the surgical robotic system component moves in a same direction as the detected object movement, and further that a predetermined desired spacing between the object and the component is maintained throughout the movement. Representative examples of the surgical robotic system component moving in parallel to the object will be described in more detail in reference to FIG. 4-6.

Returning now to FIG. 2, in FIG. 2, capacitive members 204, 206 are shown arranged in a grid like pattern. For example, capacitive members 204, 206 may include a first set of capacitive members 204 running along support member 202 in a first direction, and a second set of capacitive members 206 running along support member 202 in a second direction, for example a direction perpendicular to the first set of capacitive members 204. The first set of capacitive members 204 may, for example, be described as running vertically, or along or parallel to the y-axis. The second set of capacitive members 206 may, for example, be described as running horizontally, or along or parallel to the x-axis. Although each set of capacitive members is shown including five capacitive lines, it is contemplated that any number of members may be used depending on the desired sensitivity and/or density of the sensing assembly 200. For example, where it is desirable for sensing assembly 200 to detect a relatively small object (e.g., smaller than a fingertip) or more discrete or smaller movements, the number of capacitive members may be increased so that the area between the detection regions is reduced (e.g., size of the non-detection regions are reduced).

Arranging capacitive members 204, 206 as shown in FIG. 2 may allow for the detection of an object hovering over sensing assembly 200, and further allow for a proximity and motion of object 208 over assembly 200 within three dimensions to be determined. Representatively, when object 208 is positioned a distance over capacitive hover sensing assembly 200, the object proximity (e.g., distance to the sensing assembly) may be detected, and if the object moves along the z-axis (e.g., toward or away from the sensing assembly), such linear movement may further be detected and used to determine a location, orientation, position, and/or movement of the object with respect to sensing assembly 200. Further movement of object 208 along the x-axis can be detected by capacitive members 204 since the object will cause a capacitance change at each of the capacitive members 204 as it passes from one to the next. Similarly, movement of the object 208 along the y-axis can be detected by capacitive members 206 since the object will cause a capacitance change at each of capacitive members 206 as it passes from one to the next. In this aspect, sensing assembly 200 can detect a linear movement of the object 208 according to at least three degrees of freedom (e.g., front/back, left/right and up/down). In addition, since a location of each of capacitive members 204 with respect to capacitive members 206, as well as their location on support member 202, is known, any linear movement within the x-y plane (e.g., any movement within an x-y plane parallel to support member 202) may be detected by capacitive hover sensing assembly 200 and used to determine a location of the object. Still further, in some cases, it is contemplated that movement according to other degrees of freedom may be detected by sensing assembly. For example, sensing assembly 200 could detect a rocking or rolling of object 208 along the x-axis or the y-axis by comparing a capacitance at one or more of capacitive members 204, 206 as the object is moving. The corresponding signal output by sensing assembly 200 may, in turn, be used to cause a parallel movement of a surgical robotic system component that assembly 200 is coupled to (e.g., front/back, left/right, up/down, rock, roll, etc).

Figure 3:
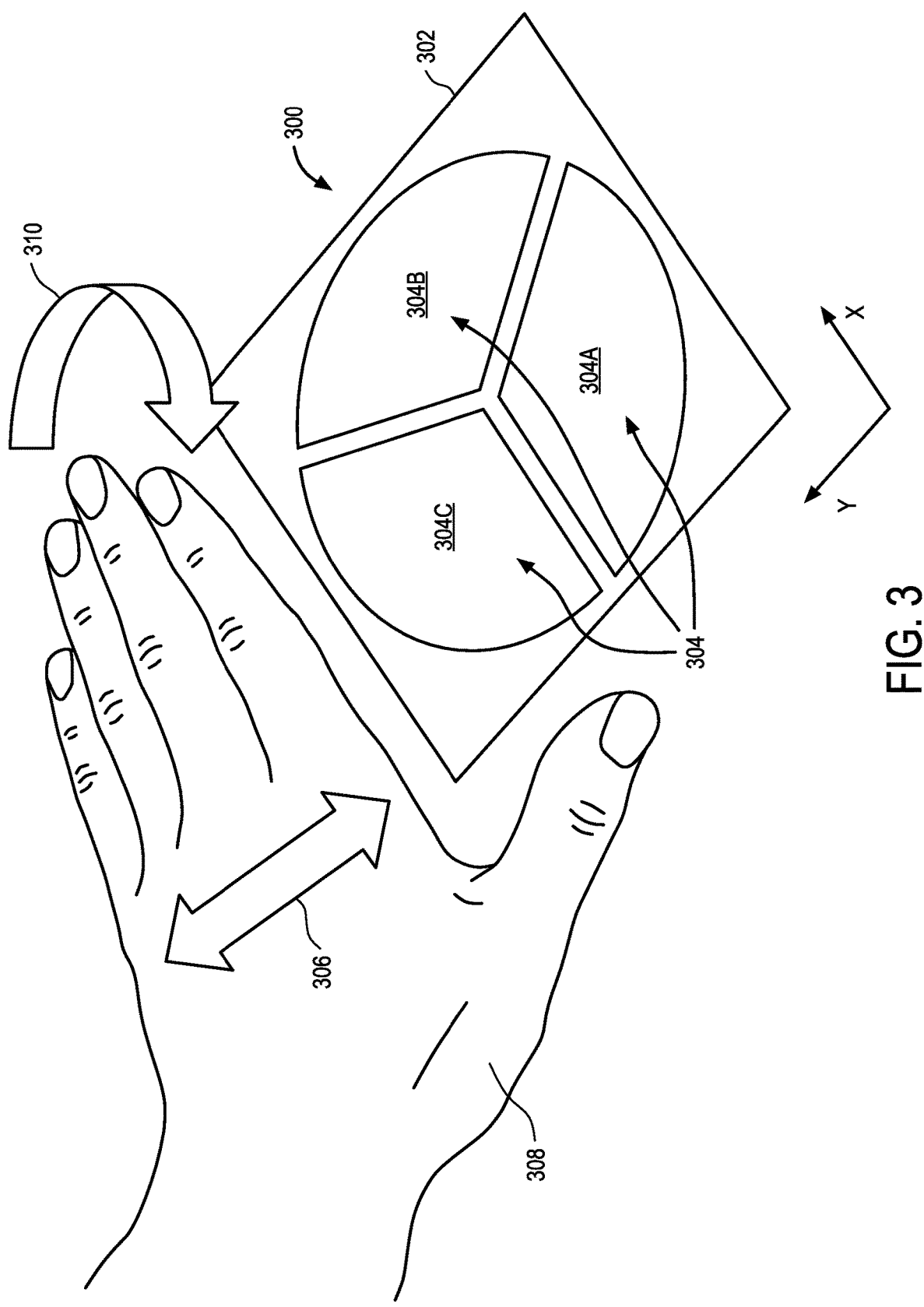
FIG. 3 is a pictorial view of a capacitive hover sensing assembly, in accordance with another embodiment.

FIG. 3 is a pictorial view of another embodiment of a capacitive hover sensing assembly that can be integrated into one or more surgical robotic system components of surgical robotic system 100. Similar to the capacitive hover sensing assembly described in FIG. 2, capacitive hover sensing assembly 300 includes a support member 302 and an arrangement of capacitive members 304. In this embodiment, however, capacitive members 304 are arranged in a circular, pie shaped pattern that allows for the detection of the object proximity and any of the previously discussed movements (e.g., a linear movement as illustrated by arrow 306), however, also allows for detection of an angular movement of the object 308, as illustrated by arrow 310. Representatively, capacitive members 304 may include capacitive members 304A, 304B and 304C which are each formed as substantially triangular shaped pieces that together make up a circular capacitive hover sensing region. Although three members 304A-304C are illustrated, it is contemplated that more or less members may be arranged in a circle as desired. Each of capacitive members 304A-304C may be made of a conductive material, which as previously discussed, can form an electrostatic field at each of the capacitive members 304A-304C upon application of a voltage. When object 308 is brought in close proximity to, or otherwise within a detection range of, the capacitive members 304A-304C, it changes the local electric field, and in turn, the capacitance at each of members 304A-304C. This change in capacitance at each of the capacitive members 304A-304C can be used to determine a linear movement 308 as previously discussed, and/or an angular motion 310 of object 308. This information may, in turn, be used to cause a parallel movement of the associate surgical robotic system component without object 308 physically touching the component. For example, an angular movement 310 may be detected as an initial hovering or presence of object 308 over capacitive members 304A, 304C, followed by a hovering of object 308 over capacitive members 304A, 304B. This may occur, for example, where initially the user's palm is positioned over capacitive member 304A and the fingers are positioned over capacitive member 304C, and the user then rotates their hand to the right as shown by arrow 310 (in the x-y plane) so that while the palm remains over capacitive member 304A, the fingers are now over capacitive member 304B and not member 304C. Capacitive hover sensing assembly 300 may detect such a movement as, for example, an initial change in capacitance at members 304A, 304C, followed by a change in capacitance at member 304B, and member 304C returning to its initial state. A corresponding signal(s) may be output by capacitive hover sensing assembly 300 to the surgical robotic system controller/processor. Based on the signal(s), the controller/processor determines the movement is a rotational movement of object 308 and causes a corresponding parallel movement of the associated surgical robotic system component (e.g., rotational movement), without the user having to physically contact the component.

Figure 4:
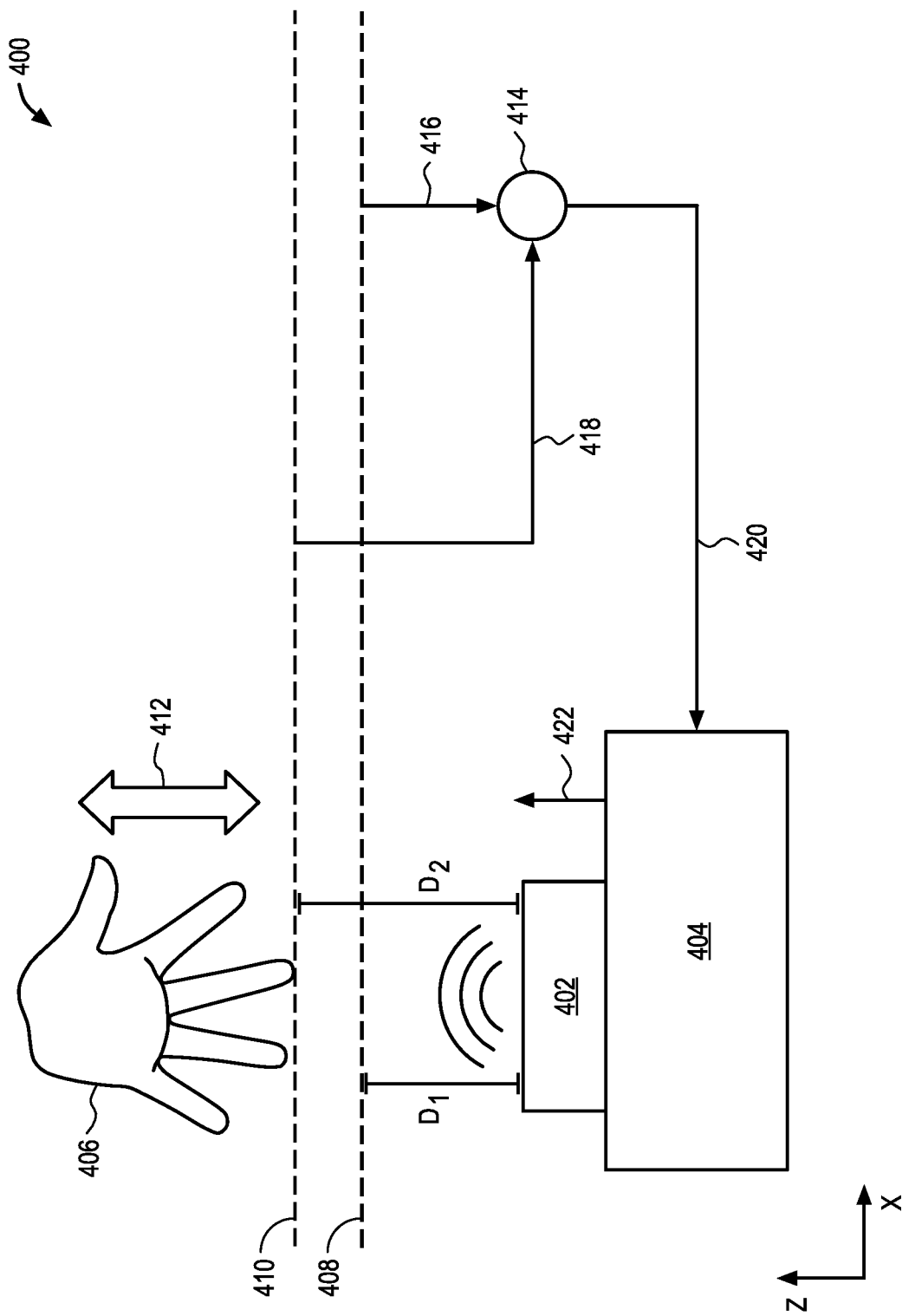
FIG. 4 is a block diagram of an exemplary process for causing a touch-free movement of a surgical robotic system component using a capacitive hover sensing assembly, in accordance with an embodiment.

FIG. 4 is a schematic illustration of a hover sensing system for causing a touch-free movement of a surgical robotic system component, according to one embodiment. Representatively, FIG. 4 illustrates a capacitive hover sensing system 400 including a capacitive hover sensing assembly 402 coupled to a surgical robotic system component 404. The capacitive hover sensing assembly 402 may include any one of the previously discussed hover sensing capacitive member arrangements. It is further contemplated that in some embodiments, the sensing assembly 402 is integrated into the surgical robotic system component 404. For example, the capacitive member(s) may be made of a conductive material that is printed directly onto a surface (i.e., support member) of the surgical robotic system component 404 into the desired arrangement or pattern, or etched into a surface of the surgical robotic system component 404. The surface could be any surface of the surgical robotic system component 404 that is easily accessible by an object used to move the component 404. For example, where the surgical robotic system component 404 is a surgical robotic arm coupled to a surgical table, the surface may be the surface of a cosmetic panel or outer shell of the surgical robotic arm that faces away from the surgical table. Alternatively, where the surgical robotic system component 404 is the surgical table, the surface may be a cosmetic panel along a side of the surgical table that the user can easily reach.

Returning now to the capacitive hover sensing system 400 illustrated in FIG. 4, it can be seen that system 400 includes a predetermined object proximity sensing or avoidance range 408 which corresponds to a desired spacing to be maintained between surgical robotic system component 404 and object 406. System 400 further includes an actual object proximity sensing range 410 which corresponds to an actual spacing between surgical robotic system component 404 and object 406. Capacitive hover sensing assembly 402 is configured to output a corresponding signal, for example output signal 418, that can be used to determine whether the desired spacing between object 406 and surgical robotic system component 404 is being maintained and/or whether it is not, and therefore the surgical robotic system component 404 needs to be moved. For example, when an object 406 is positioned over assembly 402, sensing assembly 402 detects the presence of the object 406 as a change in capacitance at any one or more of the associated capacitive members. This change in capacitance is sent as a corresponding output signal 418 to system controller 414, which in turn, uses this information to determine (e.g., measure) the actual distance (D2) between object 406 and sensing assembly 402. A predetermined distance (D1), is then compared, by the controller 414, to the actual distance (D2) detected by sensing assembly 402. The predetermined distance (D1) may be a predefined fixed value or value range 416, which represents the avoidance range 408 in the hover sensing coordinates/measurement system. This value or range 416 may be kept fixed or dynamically modulated throughout the operation, for example, depending on the measured robot movement speed. Value or range 416, corresponding to distance (D1), may be input to, and/or stored by, controller 414. The controller 414, in turn, determines whether the actual distance (D2) is the same as the predetermined distance (D1) (or within an acceptable range) or different than the predetermined distance (D1) (or outside an acceptable range). In other words, controller 414 determines whether the object 406 is at a desired spacing, farther from, or closer to, sensing assembly 402, than desired. When it is determined that distance (D1) is different than (D2) (e.g., the object has moved), controller 414 outputs a robot command signal 420 to surgical robotic system component 404 causing component 404 to move in a same direction as the object so that the actual distance (D2) matches the predetermined distance (D1). Representatively, when controller 414 determines actual distance (D2) is greater than predetermined distance (D1) (e.g., the object has moved away from the surgical robotic system component), the robotic command signal 420 causes the surgical robotic system component 404 to move in a same direction (as illustrated by arrow 422) so that it moves toward object 406 until the actual distance (D2) is once again equal to (or within an acceptable range of) the predetermined distance (D1). As long as object 406 continues to move away (e.g., in a z-direction as illustrated by arrow 412) from surgical robotic system component 404, the robotic command 420 will cause surgical robotic system component 404 to continue to move in the same direction (as illustrated by arrow 422) so that distance (D1) is maintained without object 406 ever contacting component 404. Similarly, when controller 414 determines actual distance (D2) is less than predetermined distance (D1) (e.g., object 406 is moving toward component 404), the robotic command signal 420 causes the surgical robotic system component 404 to move in a same direction (e.g., away from object 406) until the the actual distance (D2) is equal to (or within an acceptable range of) the predetermined distance (D1). As long as object 406 continues to move away from (e.g., in a z-direction as illustrated by arrow 412) surgical robotic system component 404, the robotic command 420 will cause surgical robotic system component 404 to continue to move toward object 406 so that distance (D1) is maintained. Since surgical robotic system component 404 will continue to follow or mirror the movement of object 406 so that a fixed offset distance (e.g. predetermined distance D1) is maintained, surgical robotic system component 404 is referred to herein as moving in parallel to object 406.

Figure 5:
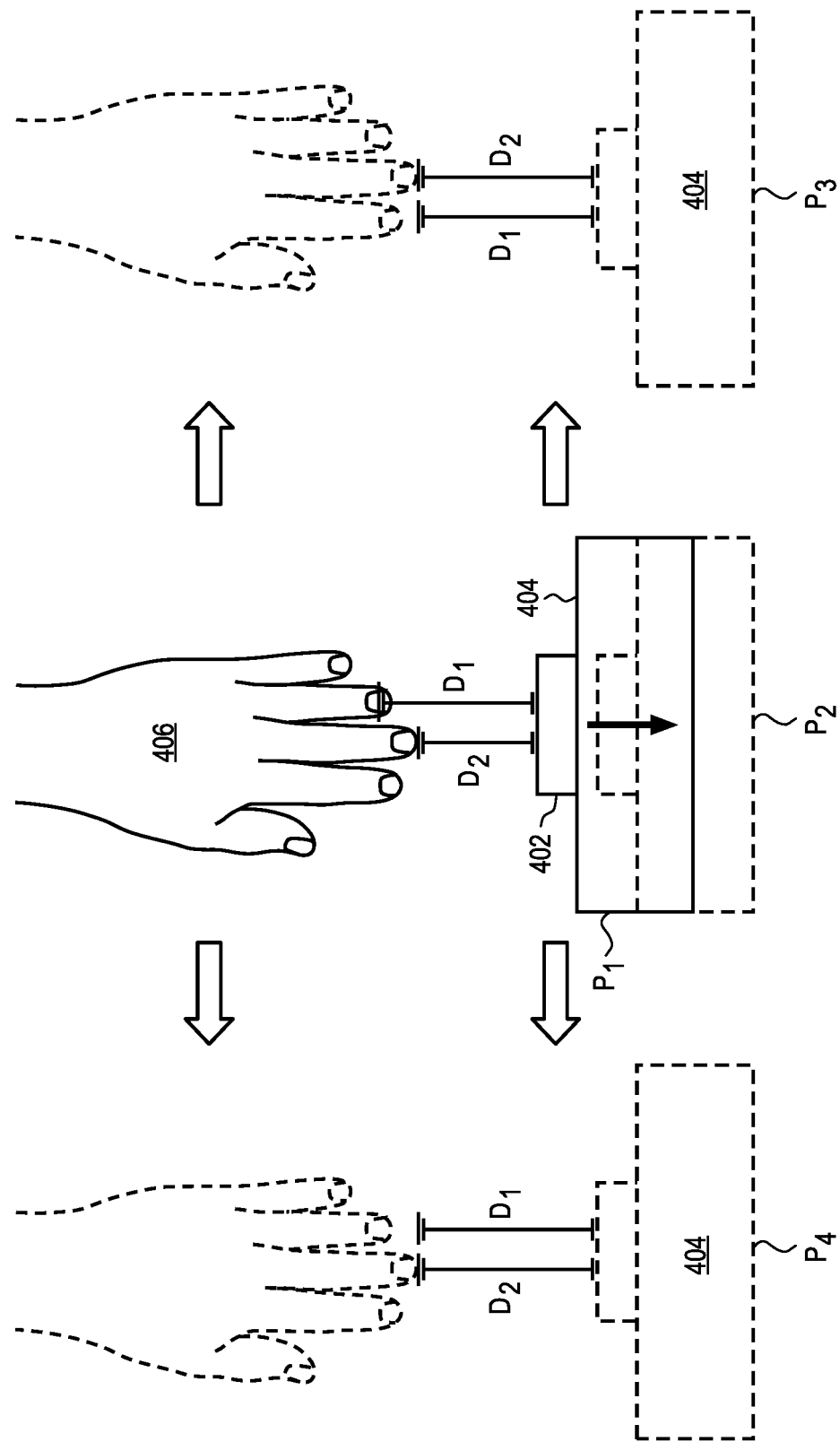
FIG. 5 is a pictorial view of an exemplary process for causing a touch-free movement of a surgical robotic system component using a capacitive hover sensing assembly, in accordance with an embodiment.

FIG. 5 is a schematic illustration of a surgical robotic system component moving in parallel to an object, as described in FIG. 4. Representatively, as can be seen from FIG. 5, when sensing assembly 402 detects that the object 406 is moving forward or backward, the surgical robotic system component 404 is caused to move forward or backward. For example, sensing assembly 402 detects that the object 406, in this case the user's finger, is at an actual distance (D2) that is different from the predetermined distance (D1). In this case, the finger is shown closer to sensing assembly 402 than desired. The controller therefore causes surgical robotic system component 404 to move away from the finger as illustrated by the arrow, for example from a first position (P1) to a second position (P2), until the actual distance D2 is equal to (or within an acceptable range) the desired predetermined distance (D1). Similarly, when an up or down motion of the object 406 is detected as shown, surgical robotic system component 404 moves in parallel to a third position (P3) or a fourth position (P4). Although not shown, a left or right motion of the object 406 may be detected in a similar manner.

Figure 6:
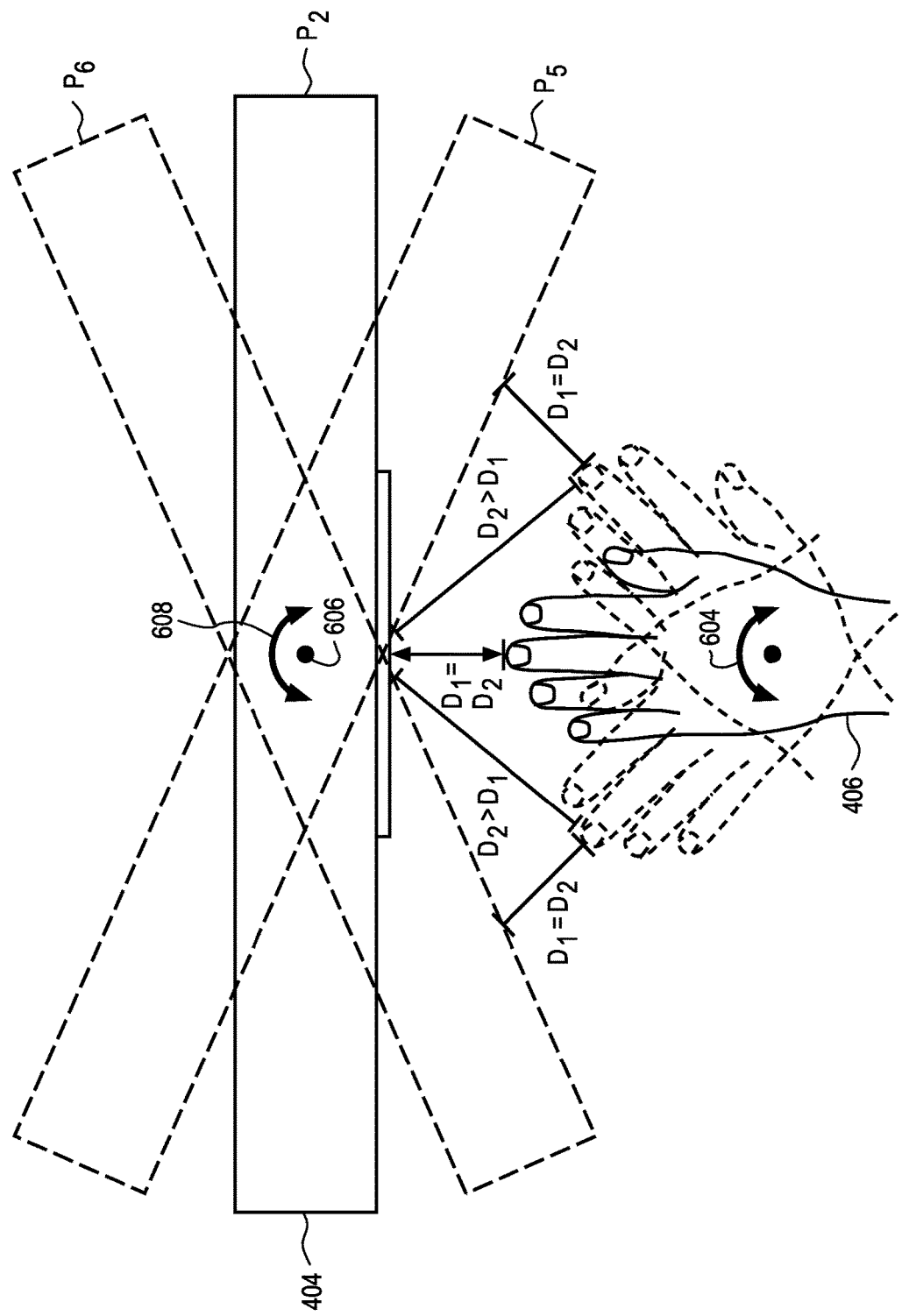
FIG. 6 is a pictorial view of an exemplary process for causing a touch-free movement of a surgical robotic system component using a capacitive hover sensing assembly, in accordance with an embodiment.

In addition, since, as previously discussed, sensing assembly 402 may include any number of capacitive members arranged to detect, for example, both linear and angular movements, the surgical robotic system component 404 can further be caused to mirror an angular movement of object 406 detected by sensing assembly 402. For example, when a rotational movement of object 406 over sensing assembly 402 (e.g., within the x-y plane as shown in FIG. 3) is detected, the controller 414 may send a robot command signal to the associated surgical robotic system component 404 causing it to move in parallel, for example to rotate about a rotational axis of the surgical robotic system component 404, as illustrated by FIG. 6. Representatively, FIG. 6 illustrates a top schematic view of object 406 and surgical robotic system component 404 in an initial position with respect to one another where object 406 is at the predetermined distance (D1), which can be predetermined or calibrated, with respect to sensing assembly 402 (e.g., position P2 in which D1=D2). When the object 406 pivots or rotates to the right or left as illustrated by arrow 604, however, the actual distance (D2) of the object 406 detected by sensing assembly 402 becomes greater than the desired predetermined distance (D1). The controller therefore sends a robotic command signal to surgical robotic system component 404 causing it to also pivot or rotate around its central axis 606, so that it moves in parallel to object 406 and maintains an actual distance (D2) that is equal to the predetermined distance (D1) (or within an acceptable range). For example, where object 406 rotates or pivots to the right as shown, surgical robotic system component 404 mirrors this movement and pivots to the fifth position (P5) so that an actual distance (D2) equal to the predetermined distance (D1) is maintained. Similarly, where object 406 rotates or pivots to the left as shown, surgical robotic system component 404 mirrors this movement and pivots to the sixth position (P6) so that an actual distance (D2) equal to the predetermined distance (D1) is maintained. It should further be understood that although an angular movement within, for example the x-y plane is shown in FIG. 6, a rocking or rolling of object 406 about an axis as previously discussed, and corresponding parallel movement of the component 404, may occur in a similar manner.

In addition, it can be understood from the foregoing description in which movement of the object according to a number of degrees of freedom (DOF) can be detected, that surgical robotic system component can be caused to change a position, pose, orientation, or the like, according to any number of degrees of freedom (DOF). Representatively, any one or more of the previously discussed operations may be used to detect the object movement and depending on the freedom of movement of the surgical robotic system component, cause the surgical robotic system component to move, for example, up/down, forward/backward, left/right, rotate, roll and/or pitch. In addition, the information detected by sensing assembly can be used to change an overall position, pose or orientation of the surgical robotic system component according to a desired trajectory, and in a smooth and continuous manner. For example, in cases where the surgical robotic system component is a surgical robotic arm having multiple arm linkages or links and joints, to follow a smooth trajectory, more than one arm joint may need to be activated at the same time with varying speeds. In addition, in some configurations, it is possible that no single arm joint is aligned in the correct orientation to provide a motion in the desired direction. The capacitive hover sensing system may therefore, in some embodiments, further be configured to determine the position and degree of freedom of each arm joint, and account for link lengths/joint limits, and manipulate each of the links/joints as necessary, to effect a touch free movement of the surgical robotic system component as required based on the information obtained from the sensing assembly.

Figure 7:
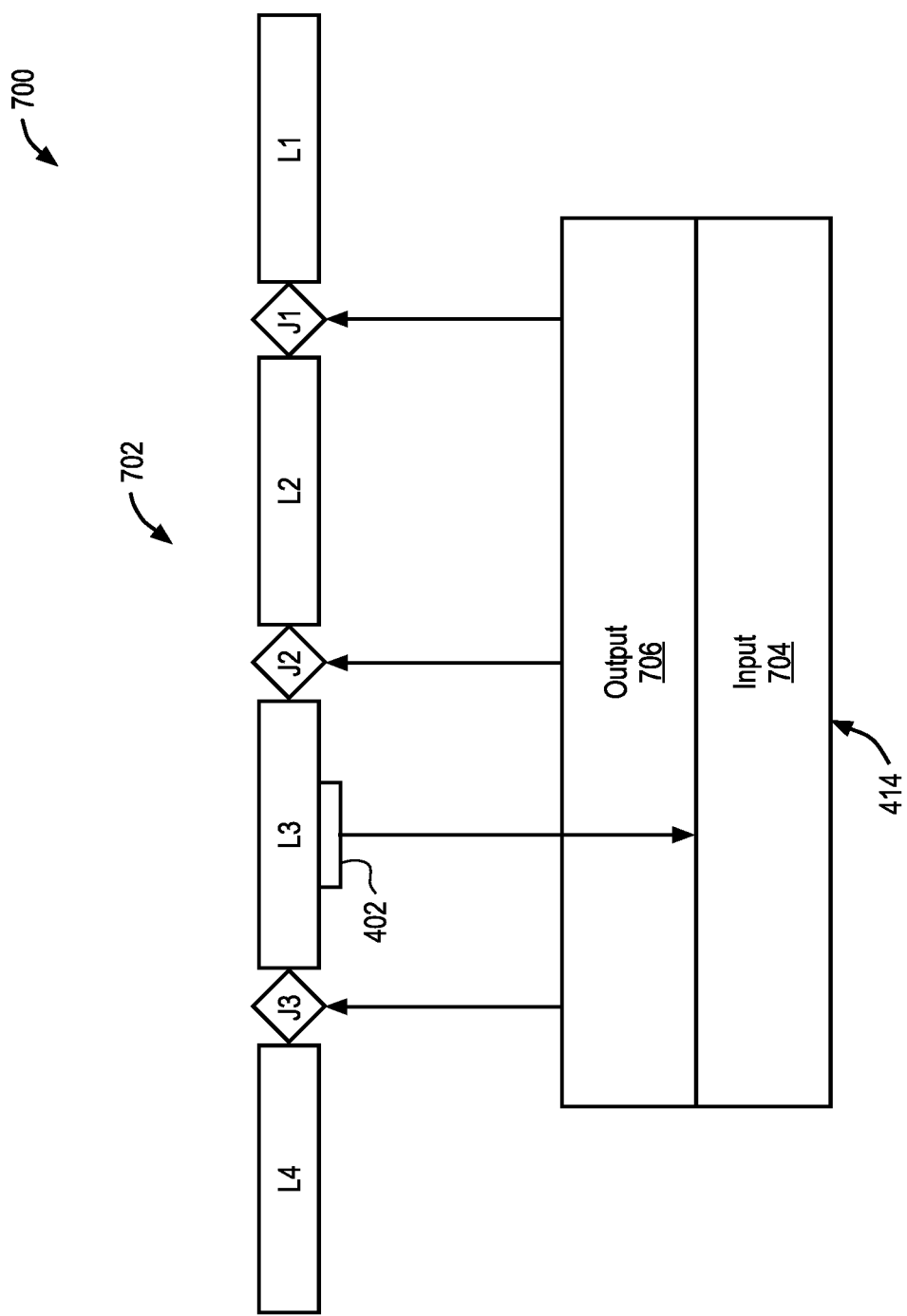
FIG. 7 is a block diagram of an exemplary process for causing a touch-free movement of a surgical robotic system component using a capacitive hover sensing assembly, in accordance with an embodiment.

FIG. 7 illustrates a representative capacitive hover sensing system configured to automatically compute a required arm joint movement and manipulate one or more arm joints based on the object movement detected by the sensing assembly. Representatively, capacitive hover sensing system 700 includes a capacitive hover sensing assembly 402 coupled to a surgical robotic arm linkage or link (L3) of a surgical robotic arm 702. Surgical robotic arm 702 is shown having a number of arm linkages or links joined together by a number of link joints. Although four arm links (L1, L2, L3 and L4) and three link joints (J1, J2 and J3) are shown, surgical robotic arm 702 may include "n" number of links and joints. In addition, although hover sensing assembly 402 is shown at arm link L3, sensing assembly 402 could be at any of arm links L1-L4. In addition, it should be recognized that link joints J1-J3 and their associated links L1-L4 may move according to multiple degrees of freedom (e.g., a up/down, right/left, forward/back, rotate, pitch or roll).

Representatively, sensing assembly 402 may detect an object hovering near arm link (L3) and a corresponding sensor signal is generated and sent to an input processing component 704 of controller 414. Input processing component 704 may determine, based on the signal from sensing assembly 402, a distance, location, position, orientation and/or movement of the object with respect to arm link (L3) specifically. In some cases, the distance, location, position, orientation and/or movement of the object may be determined by the input processing component 704 to correspond to a gesture of the user's hand, which is selected from a predetermined set of gestures stored by the controller 414. For example, the gestures could be pinching of the users fingers together, rotating or twisting the finger or hand, etc. The output processing component 706 of controller 414 may then, based on this information, determine a desired movement, location, position, orientation and/or pose of the surgical robotic arm 702 and send a robotic command signal to the surgical robotic system component 702, to manipulate the surgical robotic link L3 to achieve the desired movement, location, position, orientation and/or pose. For example, output processing component 706 may send a robotic command signal to move link joint J2, which in turn, may cause the desired movement of robotic link L3. In some cases, however, it is determined by the controller 414 that one or more of the other arm links L1, L2 or L4 and/or link joints J1 or J3 are not in the appropriate configuration to achieve the desired movement, location, position, orientation and/or pose. In such cases, the output processing component 706 further determines the position of the other arm links L1, L2 or L4 and/or joints J1 or J3 that is necessary to achieve the desired movement of robotic link L3, and sends one or more further robotic command signal(s) to these links and/or joints to move them to the configuration necessary. In this way, system 700 allows for touch-free movement of the surgical robotic arm in a smooth and continuous manner.

Figure 8:
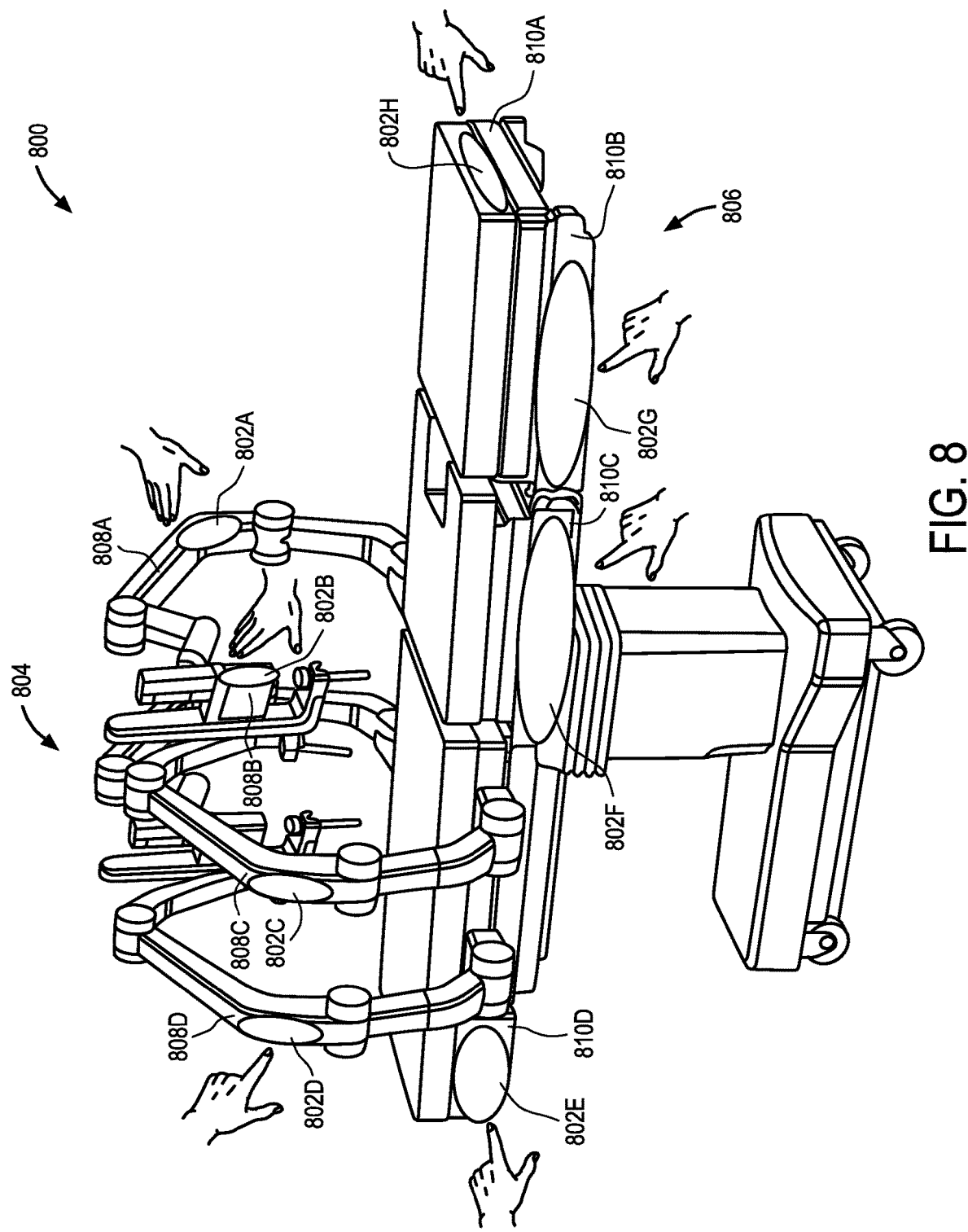
FIG. 8 is a pictorial view of an example surgical robotic system including a capacitive hover sensing assembly, in accordance with an embodiment.

FIG. 8 is a schematic illustration of a touch-free surgical robotic system having a number of surgical robotic arms attached to a surgical robotic table. In FIG. 8, it can be seen that touch-free surgical robotic system 800 includes a number of capacitive hover sensing assemblies 802A, 802B, 802C, 802D, 802E, 802F, 802G and 802H at one or more of the surgical robotic arms 804 and/or surgical table 806. Representatively, system 800 may include four surgical robotic arms 804 robotically coupled to surgical table 806. For example, two surgical robotic arms 804 positioned along one of the sides of surgical robotic table 806 and two surgical robotic arms 804 positioned along the other side of the surgical robotic table 806. Any one or more of the surgical robotic arms 804 may include a panel 808A-808D, or other surface, which forms, or is otherwise at, a portion of surgical robotic arms 804 that is easy to accessed by the user. In some cases, the panel may be formed by the support member of any one or more of assemblies 802A-802H which is shaped to form part of the outer shell of the arm.

In one aspect, panels 808A-808D may be cosmetic panels (e.g., panels visible to a user) of surgical robotic arms 804 that face away from surgical table 806. For example, panels 808A-808D may face a different direction than a longitudinal axis intersecting the surgical table 806 so that they are considered outward facing surfaces. Said another way, panels 808A-808D may face away from any one or more of the side panels 810A, 810B, 810C and/or 810D forming the perimeter of surgical table 806. In this aspect, capacitive hover sensing assemblies 802A-802D at each of panels 808A-808D can be easily reached by a user for repositioning of surgical robotic arms 804 as previously discussed. In addition, one or more of side panels 810A-810D forming surgical table 806 may include hover sensing assemblies 802E-802H. Side panels 810A-810D may, for example, be vertically oriented panels that form the perimeter around the horizontal surface of table 806 where the patient would lay. Since side panels 810A-810D face away from, for example, the horizontal surface of surgical table 806 where a patient would lay, they are also easily accessible by the user. The user may therefore simply position their hand, finger, or any other portion of their body near any one or more of capacitive hover sensing assemblies 802A-802H to move one or more portions of surgical table 806 and/or surgical robotic arms 804, as previously discussed.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A control system for surgical robots based on proximity sensing, the control system comprising:
   a proximity sensor coupled to a component of a surgical robot, the component of the surgical robot comprising a table, a robotic arm coupled to the table, or a surgical tool mounted on the robotic arm, the proximity sensor configured to sense a linear movement and an angular movement of a nearby controlling object, and wherein the proximity sensor comprises a first set of capacitive lines and a second set of capacitive lines arranged on a support member such that they are operable to detect the linear movement along an x-axis and a y-axis and the angular movement, and wherein the angular movement comprises a rotational movement about a z-axis, an x-axis, and a y-axis; and
   a processor configured to drive the component of the surgical robot to follow the linear movement or the angular movement of the controlling object sensed by the proximity sensor.

2. The control system of claim 1 wherein the linear movement is parallel to the z-axis, the x-axis or the y-axis.

3. The control system of claim 1 wherein the proximity sensor is operable to sense a movement of the nearby controlling object according to at least five degrees of freedom.

4. The control system of claim 1 wherein the component of the surgical robot is the robotic arm and the support member is a cosmetic panel of the robotic arm that faces away from the surgical table.

5. The control system of claim 4 wherein the first set of capacitive lines and the second set of capacitive lines are printed onto the cosmetic panel of the robotic arm.

6. The control system of claim 1 wherein the component of the surgical robot is the table and the support member forms a vertically oriented side panel of the table that connects to a horizontally oriented patient support surface of the table.

7. The control system of claim 1 wherein the proximity sensor further comprises a plurality of capacitive pads arranged in a circular shape, wherein the plurality of capacitive pads are configured to detect the angular movement of the controlling object around the circular shape.

8. A surgical robotic system comprising:
   a table and a surgical robotic arm coupled to the table, the surgical robotic arm comprising a plurality of robotic arm links and a plurality of joints operable to move according to multiple degrees of freedom;
   a proximity sensor printed on a cosmetic panel of at least one robotic arm link of the plurality of robotic arm links of the surgical robotic arm or the table, the proximity sensor comprising a first sensing pad, a second sensing pad and a third sensing pad each having a triangular shape and arranged in a circular shape such that they are operable to detect a linear movement and an angular movement of a nearby controlling object prior to contact with the table or the at least one robotic arm link of the surgical robotic arm; and a processor configured to drive a movement of the table or the at least one robotic arm link based on the movement of the controlling object.

9. The surgical robotic system of claim 8 wherein the linear movement of the controlling object is a movement in a direction parallel to a z-axis, an x-axis or a y-axis and the angular movement comprises a rotational movement about the z-axis, the x-axis or the y-axis.

10. The surgical robotic system of claim 8 wherein the plurality of sensing pads are capacitive sensing pads printed on the cosmetic panel of the table or the surgical robotic arm.

11. The surgical robotic system of claim 8 wherein the proximity sensor is coupled to the surgical robotic arm and the processor is operable to control the movement of the surgical robotic arm according to at least four degrees of freedom that are in parallel to the detected movement of the controlling object and maintain a same distance from the controlling object.

12. The surgical robotic system of claim 8 wherein the linear movement and the angular movement of the nearby controlling object corresponds to a gesture and the processor is operable to recognize the gesture as a predetermined gesture corresponding to a predetermined movement and cause the predetermined movement of the table or the at least one robotic arm link.

13. The surgical robotic system of claim 8 wherein the proximity sensor is coupled to the at least one robotic arm link, and the processor is operable to cause a movement of the at least one robotic arm link based on the movement of the controlling object, and the processor is further operable to cause another robotic arm link of the plurality of robotic arm links to move based on the at least one robotic arm movement to achieve a desired overall position of the robotic arm.

14. The surgical robotic system of claim 8 wherein the processor causes the table or the surgical robotic arm to maintain a same distance from the controlling object by measuring an actual distance between the table or the surgical robotic arm and the controlling object and comparing the actual distance to a predetermined distance, and when the actual distance is different than the predetermined distance, sending a robotic command signal to the table or the surgical robotic arm causing the table or the surgical robotic arm to move in the same direction as the controlling object until the actual distance is the same as the predetermined distance.

15. A method for touch-free control of a surgical robot component based on proximity sensing, the method comprising:

determining a distance between a user and a surgical robot component using a proximity sensor comprising a first set of capacitive lines and a second set of capacitive lines coupled to the surgical robot component;

comparing the determined distance of the user to a predetermined target distance, the predetermined target distance being a desired distance to be maintained between the user and the surgical robot component; and automatically causing the surgical robot component to move linearly in a direction parallel to an x-axis, a z-axis, or a y-axis or angularly in a rotational movement about the x-axis, the z-axis or the y-axis based on the comparing so that the determined distance is equal to the predetermined target distance prior to the user contacting the surgical robot component.

16. The method of claim 15 wherein the linear movement and the angular movement are detected based on a change in capacitance at one or more of the first set of capacitive lines and the second set of capacitive lines.

17. The method of claim 15 wherein the surgical robot component is a robotic arm and the robotic arm is caused to move according to a number of degrees of freedom so that the determined distance is equal to the predetermined target distance.

18. The method of claim 15 wherein the surgical robot component is caused to move in a same direction as the user so that the determined distance is equal to the predetermined target distance.

\* \* \* \* \*